United States Patent [19]

Long

[11] 3,989,596

[45] *Nov. 2, 1976

[54] AGGREGATE OF DRIED FLOCCULATED CELLS

[75] Inventor: Margaret E. Long, Winston-Salem, N.C.

[73] Assignee: R. J. Reynolds Tobacco Company, Winston-Salem, N.C.

[ * ] Notice: The portion of the term of this patent subsequent to June 28, 1991, has been disclaimed.

[22] Filed: Oct. 14, 1975

[21] Appl. No.: 621,995

Related U.S. Application Data

[62] Division of Ser. No. 455,696, March 28, 1974, abandoned, which is a division of Ser. No. 161,337, July 9, 1971, Pat. No. 3,821,086.

[52] U.S. Cl. .................................. 195/56; 195/59
[51] Int. Cl.² ....................... C12B 1/26; C12K 1/10
[58] Field of Search ............... 195/31 F, 68, 63, 65, 195/99, 56, 59, 100, 116; 210/75, 195, 18

[56] References Cited

UNITED STATES PATENTS

| 3,356,609 | 12/1967 | Bruemmer | 210/18 |
| 3,645,848 | 2/1972 | Lee et al. | 195/31 F |
| 3,694,314 | 9/1972 | Lloyd et al. | 195/31 F |
| 3,821,086 | 6/1974 | Lee et al. | 195/65 X |

*Primary Examiner*—A. Louis Monacell
*Assistant Examiner*—Thomas G. Wiseman
*Attorney, Agent, or Firm*—Manford R. Haxton; Herbert J. Bluhm

[57] ABSTRACT

Microbial cells having active enzymes associated therewith are subjected to flocculation conditions to produce a flocculated whole cell aggregate that is subsequently dried. The dried aggregate is useful in effecting enzyme-catalyzed chemical transformations. Substrates are brought into contact with the flocculated cell aggregates where they undergo chemical transformations in the presence of active enzymes associated with the cells.

22 Claims, No Drawings

[3,989,596]

AGGREGATE OF DRIED FLOCCULATED CELLS

This is a division of application Ser. No. 455,696 filed Mar. 28, 1974, now abandoned, which, in turn, is a division of application Ser. No. 161,337, filed July 9, 1971, now U.S. Pat. No. 3,821,086.

SUMMARY OF THE INVENTION

This invention relates to a process for effecting transformation of various substrates in the presence of microbial cells containing active enzymes. More specifically, this invention relates to the use of microbial cells in enzymatic processes wherein the cells are adapted for use in batch or continuous-type processes by subjecting them to flocculation techniques.

BACKGROUND OF THE INVENTION

The use of enzymes derived from microbial cells to effect specific chemical transformations is well known. In carrying out such transformations, cell-free preparations are commonly employed in batch-type processes. The enzymes are usually liberated from the cell by mechanical means or by autolysis but this is an expensive process which often leads to additional technical problems as well as to questions of economic feasibility. The use of whole cells is also generally avoided because they do not lend themselves to continuous industrial scale processes.

Various difficulties encountered with the use of whole cells as well as cell-free enzymes have led in recent years to an increased interest in the preparation of various forms of immobilized enzymes. Such immobilized enzymes can be used in a batch-wise process as well as in a continuous column process. The use of immobilized enzymes requires separation of the enzyme from the microorganism, purification and attachment to support materials such as dextran or cellulose derivatives, organic resins and glass beads. The processes of extraction, purification and insolubilization are time consuming and are usually accompanied by a substantial loss of initial enzyme activity.

It has long been known that insoluble materials such as cells are more efficiently removed from liquids by the use of polyelectrolytes, natural gums or alum. For example, fermentations involving extracellular enzymes commonly use polyelectrolytes to aid in the removal of the unwanted cells and improve clarity of the enzyme-containing filtrate. Some of the mechanistic aspects associated with the polyelectrolyte flocculation of bacteria are presented by P. L. Busch and W. Stumm in Environmental Science and Technology, 2, 49–53 (January, 1968) as well as by L. L. Gasner and D. I. C. Wang in Biotechnology and Bioengineering 12, 873–887 (1970).

DETAILED DESCRIPTION

The present invention provides a convenient and effective means of adapting enzymes for use in either continuous- or batch-type processes by the use of flocculated microbial cells having the desired enzyme activity. The method disclosed herein makes separation of the enzyme from the microorganism unnecessary. This, in turn, obviates the need for any enzyme purification or insolubilization procedures. Although this invention may be applied to any microorganism, it is particularly suited to those organisms producing intracellular enzymes useful in effecting specific transformations of substrates.

As mentioned previously, the flocculation of microbial cells has received considerable attention in recent years primarily in connection with biological waste treatment and clarification of fermentation liquors. It has now been found that whole microbial cells which have been formed into aggregates by the use of suitable flocculating agents may be used directly in a wide variety of enzymatic processes. Quite unexpectedly, it has been discovered that subjecting flocculated microbial cells to dehydrating conditions imparts a certain rigidity or structural integrity to the flocculated cells without impairing the enzyme activity thus resulting in a material that is particularly adaptable to use in continuous- or batch-type enzymatic processes. For example, a bed of flocculated microbial cells prepared in accordance with the teachings of this invention is able to withstand repeated passage of substrate solutions through the bed with retention of satisfactory flow rates and enzyme activity for extended periods of time.

A variety of flocculating agents are useful in promoting the desired cell aggregation. Such agents include anionic polyelectrolytes such as carboxyl-substituted polyacrylamides, polystyrene sulfonates and polycarboxylic acids; cationic polyelectrolytes such as polyamines, polyethyleneimine and cationic polyacrylamides; polyacids such as polylysine; and mineral hydrocolloids such as activated silicate and colloidal clay. Combinations of two or more flocculants may be used in effecting the desired aggregation. Selection of the proper flocculating agent in a given instance is easily determined by adding various agents to small samples of the cell-containing broth and comparing the texture and appearance of the cell aggregates formed. The use of filter aids and polymeric adsorbents in conjunction with the flocculating agents may be advantageous in some instances. For example, amberlite polymeric adsorbents such as acrylic esters and filter aids such as diatomaceous earth and asbestos are effective when added to the broth at the time of flocculation. Amounts of adsorbent or filter aid used may range up to 100 percent by weight based on the weight of wet cells in the broth. The present invention is not limited to the above-listed agents since similar materials would be expected to give equally satisfactory results.

Addition of flocculant to the cell-containing broth is most conveniently carried out in the form of a solution or suspension. It may also be necessary to adjust the pH of the flocculant solution and/or the broth prior to mixing. This will depend on the microorganism used, the stability of the enzyme of interest and the pH range in which the flocculant is most effective. Flocculation is preferably conducted at ambient temperatures and the quantity of flocculant required is generally 1 to 50% by weight based on the weight of the wet cells contained in the broth.

Agitation of the flocculant-containing fermentation broth must be vigorous enough to cause relatively complete exposure of the cells to the flocculant. Excessive agitation is to be avoided, however, since this tends to break down the size of the aggregates already formed thus defeating the purpose of the flocculant. Careful control of the agitation gives cell aggregates which agglomerate in the fermentor and facilitates virtually complete recovery of the available cells by standard techniques such as decantation, filtration and centrifugation.

The harvested flocculated cells may be used in a contemplated enzymatic process without further treatment; however, the useful life of such cell material in a continuous column operation is reduced considerably due to packing and settling of the material which affects the flow rates adversely. It is preferable, therefore, to dry the flocculated cells prior to use in an enzymatic process. Such treatments serve not only to enhance the substrate solution flow rates but also to improve the handling and storage properties of the flocculated cells.

The consistency of the harvested flocculated cells is such that the material may be extruded into various shapes suitable for use in an enzymatic process. The extruded cell aggregates may be used in conjunction with inert support materials in preparing packed columns for continuous operation or the extrudate may be dried prior to use.

Drying of the flocculated cells is particularly useful because it permits milling of the dried material and selection of particle sizes by sieving the milled cells. Control of particle size, in turn, insures a uniform bed when the material is packed into columns for continuous flow of substrate solutions through the packed bed. Drying of the flocculated cells also permits storage of the dried material at ambient temperatures for extended periods of time. The drying procedure may be carried out in any convenient manner such as by forced draft oven, vacuum, drum dryer, etc., provided that the drying temperatures and times used do not result in appreciable denaturation of the desired enzyme. Drying times will vary but it is preferred that the drying process be continued until the material is sufficiently brittle to permit milling.

The flocculated cells may be used for a wide variety of enzyme-catalyzed transformations such as isomerization, oxidation, dehydrogenation, hydrolysis and reduction. The material is adaptable to either batch or continuous operations although transformations involving the liberation of a gas are somewhat less amenable to continuous column processes. The quantity of cell material required for a given process will depend on a number of factors including the specific enzyme activity of the material and its availability to the substrate as well as the rate and degree of transformation desired. In continuous column operations the dimensions of the column and the flow rates desired will also influence the quantity of cell material required.

The substrate, preferably in the form of a solution or emulsion, is contacted with the flocculated cell material for a time sufficient to effect the desired transformation. Operating parameters such as temperature, pH and substrate concentration are determined by the stability and conditions for optimum activity displayed by the enzyme responsible for the transformation. The product of the transformation is recovered by any suitable means or subjected to further treatment as desired.

The invention can best be illustrated by referring to a specific organism and enzyme. A selected strain of Arthrobacter such as NRRL B-3724, NRRL B-3725, NRRL B-3726, NRRL B-3727 or NRRL B-3728 is cultivated in a sterile medium containing sources of carbohydrate, nitrogen and inorganic salts. The fermentation is carried out at 30° C. in the manner described in copending application, U.S. Ser. No. 877,474 filed on Nov. 17, 1969, now U.S. Pat. No. 3,645,848. Fermentation is allowed to proceed until maximum isomerase activity is attained as determined by standard assay methods. At this point the wet cells suspended in the broth usually constitute about 4% by weight of the total broth. A polyvinylimidazoline such as Primafloc C-7 (a cationic flocculant available from Rohm and Haas of Philadelphia, Pa.) is added to the broth in the form of a 2% aqueous solution whose pH has been previously adjusted to 5.0. The amount of flocculant added is approximately 0.25% by weight based on the total broth and the addition is effected with gentle agitation of the broth. Formation of the whole cell aggregates is usually complete within 10–15 minutes. Agitation is then stopped and the flocculated cell mass settles to the bottom of the fermentor. The cells are harvested by decanting most of the clear broth and subjecting the wet flocculated cells to vacuum filtration. The harvested flocculated cells are extruded and then dried at 55° C. prior to use in a column for continuous glucose isomerization.

A glucose solution in concentrations ranging up to 50 weight percent containing sufficient $Mg^{++}$ to obtain maximum isomerization and adjusted to about pH 6 to 10 is passed through the packed column. The column is preferably heated to about 50°–75° C. to increase the rate of conversion of glucose to fructose and to inhibit growth of any contaminating organisms. The flow rate of the effluent stream is controlled so as to give glucose to fructose conversions of 40–45 percent. The degree of glucose to fructose conversion obtainable by the process of this invention ranges up to 50 percent. Two or more packed columns may be operated in series if desired and the packed cells may be recovered from the columns for subsequent use in glucose isomerizations. The isomerase activity is retained even when the cell material is recovered and refrigerated, frozen or dried prior to reuse.

Isomerization of glucose to fructose may also be effected by various species of Streptomyces which have been flocculated. Species which are useful for this purpose include S. albus, S. echinatur, S. achromogenes, S. phaeochromogenes, S, flavovirens and S. olivaceus. Flocculation of whole cells obtained from the cultivation of various species of Streptomyces is effected in a manner analogous to that described for Arthrobacter and the isomerization is also carried out similarly.

The following examples will further illustrate the application of this invention.

EXAMPLE 1

A species of Arthrobacter such as NRRL B-3728 is placed in a sterilized growth medium containing 2% dextrose, 0.3% meat protein, 0.1% yeast extract, 0.6% $(NH_4)_2HPO_4$, 0.2% $KH_2PO_4$ and 0.01% $MgSO_4.7H_2O$. The pH of the resulting medium is 6.9. Fermentation is allowed to proceed with agitation at 28° C. for 60 hours at the end of which time the pH of the broth is approximately 5.5. To this broth is added a 2% (weight per volume) solution of a suitable polyelectrolyte such as Primafloc C-7 to give a final polyelectrolyte concentration of 0.25% (weight per volume). The pH of the polyelectrolyte solution is first adjusted to about 5.0 and the fermentation broth is slowly agitated during addition of the polyelectrolyte. If desired, a filter aid such as Celite 545 (available from Johns-Manville of Baltimore, Md.) is added to the broth at a concentration of about 0.5 percent (weight per volume) just prior to addition of the polyelectrolyte solution. Gentle agitation of the broth containing the polyelectrolyte (and filter aid, if added) is continued until stable cell aggregates are formed (approximately 10 minutes). The agitation is then stopped and the cell aggregates are allowed to agglomerate thus allowing most of the clear broth to be separated from the cell material. The cell material is then collected by vacuum filtration or other suitable means. The harvested cell aggregates are dried at 55° C. before use. Isomerase activity of the harvested aggregates, as determined by standard assay methods, is comparable to the enzymatic activity of cells isolated from the fermentation broth prior to treatment with the flocculant and filter aid. Moreover, an assay of the separated fermentation broth shows no isomerase activity indicating complete recovery of the isomerase by the flocculating technique.

EXAMPLE 2

This example illustrates the preparation of dried flocculated cells and the use of the dried cells in continuous column type isomerization of glucose to fructose.

Flocculation is obtained by the combined use of a cationic and an anionic flocculating agent. Five parts of fresh Arthrobacter culture (pH 5.6) are treated with one part of a 1% (weight per volume) solution of cationic Primafloc C-7. The broth containing the flocculant is slowly stirred until large cell aggregates are formed. One part of a 1% (weight per volume) anionic Primafloc A-10 (an anionic flocculant available from Rohm and Haas) solution is then added and stirring is continued until the large aggregates break into fine particles. The flocculated cells are allowed to agglomerate as in Example 1. The cleared broth is separated and the flocculated cells are recovered by simple vacuum filtration. The pH of both flocculating solutions is adjusted with caustic before adding to the broth. The cationic Primafloc C-7 solution is adjusted to pH 5 and the anionic Primafloc A-10 is adjusted to pH 7. The final pH of the flocculated culture is about 5.6.

The filtered cell cake is extruded through a suitable die before drying the extrudate in a forced draft oven for about 24 hours at approximately 55° C. The dried cell material is granulated in a mill and sieved to 20–40 mesh. The granulated dried cells are packed into a column and glucose isomerization is carried out. The packed column is heated to 60° C. and a 2 M solution of glucose having a pH of 8.0 and containing 0.004 M $MgCl_2 \cdot 6H_2O$ is passed through the column at flow rates which are regulated to give the degree of glucose conversion desired. Conversions ranging up to 50 percent are attainable by this process.

EXAMPLE 3

*Aspergillus niger* is cultivated in a nutrient medium containing glucose, fructose, $MgSO_4 \cdot 7H_2O$, $KH_2PO_4$, $(NH_4)_2HPO_4$, urea and corn steep liquor. At the end of the fermentation period a cationic polyelectrolyte equivalent to 0.3% by weight based on the volume of the broth is added to the medium. Sufficient agitation is effected to produce aggregation of the cells. The flocculated cells are harvested and packed into a jacketed column of suitable size. The packed column is heated to 40° C. and a 5% solution of invert sugar is passed through the column to give an effluent containing gluconic acid and fructose.

EXAMPLE 4

*Streptomyces olivaceus*, strain NRRL B-3583, is cultivated in a nutrient medium containing 0.7% xylose, 0.3% dextrose, 0.5% beef extract, 0.25% yeast extract, 1.0% peptone, 0.5% NaCl, 0.05% $MgSO_4 \cdot 7H_2O$ and 0.024% $CoCl_2 \cdot 6H_2O$. The fermentation is allowed to proceed at 28° C. for 24 hours. A 2% (weight per volume) solution of a cationic polyelectrolyte is added to the fermentation broth in amounts equivalent to 0.05% (weight per volume) of the dry flocculant. The broth is briefly agitated to promote aggregation of the cells. Agitation is then stopped and sedimentation of the flocculated cells is allowed to proceed. The cell aggregates are harvested in a manner analogous to that described in Example 1. The flocculated cells are dried at 60° C. for 24 hours before subjecting the dried cell mass to gentle mechanical crushing action to reduce to particle sizes suitable for column operation. The crushed cell material is poured into a jacketed column partially filled with a 1.0 M glucose solution. The packed column is heated to 70° C. and a 1.0 M glucose solution containing 0.04 M $MgCl_2 \cdot 6H_2O$ adjusted to pH 8 is passed through the column to give conversion of glucose to fructose.

EXAMPLE 5

*Saccharomyces cerevisiae* is cultivated in a nutrient medium containing molasses. After a suitable fermentation period, a polyelectrolyte solution is added to the broth with sufficient agitation to effect aggregation of the cells. The flocculated cell mass is harvested and used in a continuous column operation wherein the column temperature is 60° C. and a 0.5 M solution of sucrose with pH 5.0 is passed through the column and sucrose is converted to invert sugar.

EXAMPLE 6

*Aspergillus oryzae* is cultivated in a nutrient medium containing wheat bran mixed with additional carbohydrates, minerals and buffering substances. Fermentation is allowed to proceed for 48 hours at 30° C. at the end of which time a solution of a suitable polyelectrolyte is added to the broth. The resulting aggregation of the flocculated cells is aided by gentle agitation. The flocculated cells are harvested by decantation and filtration. The flocculated cells are then placed in a jacketed column and heated to 50° C. A neutral 0.2 M solution of acetyl-DL-methionine containing $5 \times 10^{-4}$ M $Co^{++}$ is passed through the column to give an effluent containing L-methionine.

The advantages of the invention are readily apparent from the foregoing. It will be appreciated that any number of variations in the basic process described herein may be made. Those modifications and equivalents which fall within the spirit of the invention and scope of the appended claims are to be considered part of the invention.

What is claimed is:

1. An enzyme-containing aggregate capable of effecting enzymatic transformation of a substrate contacted therewith comprising microbial cells having said enzyme associated therewith flocculated with at least one percent by weight based on the wet weight of said cells of a synthetic polyelectrolyte flocculating agent wherein said aggregate is dried and said agent is selected from the group consisting of anionic and cationic polyelectrolytes.

2. An aggregate according to claim 1 which has been extruded prior to drying.

3. An aggregate according to claim 1 which has been milled.

4. An aggregate according to claim 3 which has been sieved.

5. An aggregate according to claim 1 in which the aggregate is dried and granular in form.

6. An enzyme-containing aggregate capable of effecting enzymatic transformation of a substrate contacted therewith comprising microbial cells having a glucose-isomerizing enzyme associated therewith flocculated with a synthetic polyelectrolyte flocculating agent wherein said aggregate is dried and said agent is selected from the group consisting of anionic and cationic polyelectrolytes.

7. An aggregate according to claim 6 in which the microbial cells belong to the genus Arthrobacter.

8. An aggregate according to claim 6 in which the microbial cells belong to the genus Streptomyces.

9. A dried aggregate according to claim 6 which contains both a cationic and an anionic polyelectrolyte.

10. A dried aggregate according to claim 6 which has been extruded prior to drying.

11. A dried aggregate according to claim 6 which has been milled.

12. A dried aggregate according to claim 11 which has been sieved.

13. An aggregate according to claim 6 which is dried and granular in form.

14. An enzyme-containing aggregate capable of effecting enzymatic transformation of a substrate contacted therewith comprising microbial cells having glucose isomerase associated therewith flocculated with a synthetic polyelectrolyte flocculating agent selected from the group consisting of anionic and cationic polyelectrolytes, and wherein said aggregate is extruded and dried.

15. A dried aggregate according to claim 1 which contains both a cationic and an anionic polyelectrolyte.

16. An aggregate according to claim 2 which is dried and granular in form.

17. A dried aggregate according to claim 1 in which the microbial cells belong to the genus Arthrobacter.

18. A dried aggregate according to claim 1 in which the microbial cells belong to the genus Streptomyces.

19. A dried aggregate according to claim 1 which has been milled and sieved.

20. An aggregate according to claim 6 which contains both a cationic and an anionic polyelectrolyte.

21. An aggregate according to claim 7 in which the microbial cells belong to the genus Arthrobacter.

22. An aggregate according to claim 8 which is dried and granular in form.

* * * * *

UNITED STATES PATENT OFFICE
CERTIFICATE OF CORRECTION

Patent No. 3,989,596                   Dated November 2, 1976

Inventor(s)    MARGARET E. LONG

It is certified that error appears in the above-identified patent and that said Letters Patent are hereby corrected as shown below:

In line 1 of each of claims 15, 17, 18 and 19 the reference numeral "1" should read --14--.

In line 1 of claim 16 the reference numeral "2" should read --15--.

In line 1 of claim 20 the reference numeral "6" should read --19--.

In line 1 of claim 21 the reference numeral "7" should read --20--.

In line 1 of claim 22 the reference numeral "8" should read --21--.

Signed and Sealed this

Twenty-second Day of February 1977

[SEAL]

Attest:

RUTH C. MASON
*Attesting Officer*

C. MARSHALL DANN
*Commissioner of Patents and Trademarks*